United States Patent [19]

Sato

[11] Patent Number: 5,681,348
[45] Date of Patent: Oct. 28, 1997

[54] ENDOSCOPE-SPECIFIC THERAPEUTIC INSTRUMENT

[75] Inventor: Yukio Sato, Kodaira, Japan

[73] Assignee: Olympus Optical Co., Ltd., Tokyo, Japan

[21] Appl. No.: 388,407

[22] Filed: Feb. 14, 1995

[30] Foreign Application Priority Data

Mar. 31, 1994 [JP] Japan ................................. 6-064235
Nov. 28, 1994 [JP] Japan ................................. 6-293275

[51] Int. Cl.⁶ ............................... A61B 17/28; A61B 17/32
[52] U.S. Cl. ........................... 606/205; 606/174; 128/751
[58] Field of Search ............................ 606/1, 167, 170, 606/171–174, 205–211, 45–50; 128/749–754

[56] References Cited

U.S. PATENT DOCUMENTS

| | | | |
|---|---|---|---|
| 3,840,003 | 10/1974 | Komiya .............................. | 606/174 |
| 4,669,471 | 6/1987 | Hayashi . | |
| 5,035,248 | 7/1991 | Zinnecker . | |
| 5,137,013 | 8/1992 | Chiba et al. ....................... | 606/205 |
| 5,251,638 | 10/1993 | Cottone et al. .................... | 606/206 |
| 5,312,434 | 5/1994 | Crainich ............................. | 606/207 |
| 5,370,659 | 12/1994 | Sakashita .......................... | 606/205 |
| 5,392,789 | 2/1995 | Slater et al. ....................... | 606/205 |

FOREIGN PATENT DOCUMENTS

| | | |
|---|---|---|
| 2-141424 | 11/1990 | Japan . |
| 3-56415 | 5/1991 | Japan . |
| 5-15915 | 3/1993 | Japan . |
| 5-60752 | 9/1993 | Japan . |

*Primary Examiner*—Glenn Dawson
*Attorney, Agent, or Firm*—Armstrong, Westerman, Hattori, McLeland & Naughton

[57] ABSTRACT

An endoscope-specific therapeutic instrument includes a pair of treatment tools, a sleeve having a slit in which the pair of treatment tools are held, and a pivot pin for linking the pair of treatment tools held in the sleeve with the sleeve so that they can pivot freely. Both ends of the pivot pin lie in recesses having smaller diameters than a surface of the sleeve so as not to protrude beyond the outline of the sleeve.

16 Claims, 10 Drawing Sheets

ENDOSCOPE-SPECIFIC THERAPEUTIC INSTRUMENT

BACKGROUND OF THE INVENTION

1. Field of the Invention

The present invention relates to an endoscope-specific therapeutic instrument which is inserted in a body cavity and whose treatment unit formed as a distal part thereof is moved by manipulating an operation unit formed as a proximal part thereof.

2. Description of the Related Art

In recent years, endoscopes having an elongated insertion unit thereof inserted in a body cavity and thus enabling observation of an intracavitary organ have been widely adopted. For these kinds of endoscopes biopsy forceps, clamp forceps, or the like are available as an endoscope-specific therapeutic instrument which is used to collect living tissues or perform various treatments on lesions. The endoscope-specific therapeutic instrument including the biopsy forceps is inserted in a body cavity through a therapeutic instrument channel or inserted in an abdominal cavity by means of a trocar and cannula associated with an endoscope.

Japanese Unexamined Utility Model Publication No.2-141424 or Japanese Patent Laid-Open No.5-60752 have disclosed an endoscope-specific therapeutic instrument used to collect living tissues or treat lesions. Japanese Unexamined Utility Model Publication No.3-56415 has disclosed biopsy forceps as an endoscope-specific therapeutic instrument. Japanese Unexamined Utility Model Publication No.5-15915 has disclosed clamp forceps as an endoscope-specific therapeutic instrument.

The above endoscope-specific therapeutic instruments are elongated so as to run through a body cavity. A pair of treatment members having biopsy cups that act as a treatment unit and are opened or closed freely or a pair of clamp members are included as the distal part of the endoscope-specific therapeutic instrument. An operation unit for use in opening or closing the treatment unit composed of the pair of treatment members is formed as the proximal part of the endoscope-specific therapeutic instrument. The treatment unit and operation unit are joined by means of an operation wire. When a surgeon manipulates the operation unit, the operation wire advances or withdraws in an axial direction. This causes the treatment unit formed as the distal part to open or close.

Figure 1A:
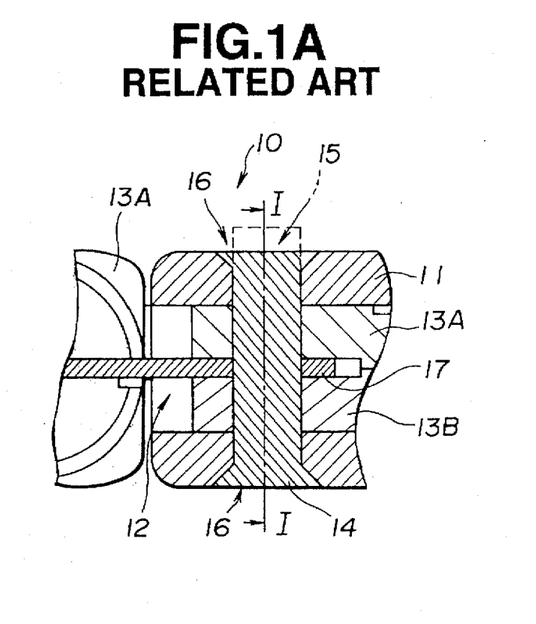
Figure 1B:
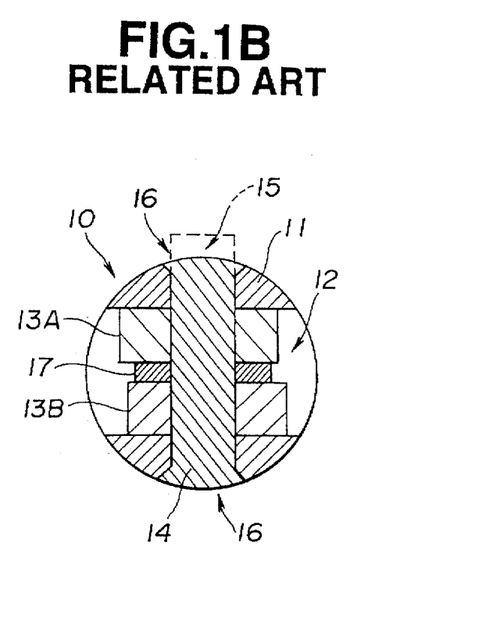

An endoscope-specific therapeutic instrument shown in FIGS. 1A and 1B has, for example, biopsy cups as a treatment unit 10. A pair of treatment members 13A and 13B having biopsy cups are held in a slit 12 formed in a substantially cylindrical sleeve 11. A pivot pin 14 is fitted into through holes bored in the treatment members 13A and 13B as well as the sleeve 11. The tip 15 of the pivot pin that is depicted with a dashed line and protruding beyond the outer surface of the sleeve 11 is caulked using a hammer, caulking jig, or laser. Thus, both ends of the pivot pin 14 are formed as caulked sections 16. The treatment members 13A and 13B are linked with the sleeve 11 so that they can pivot freely.

The caulked sections 16 formed as both ends of the pivot pin 14 are finished by filing down the caulked sections 16, so that the outlines of the caulked sections 16 match the curved outer surface of the sleeve or that the caulked sections 16 do not protrude beyond the outer surface of the sleeve 11. Reference numeral 17 denotes a needle for use in positioning and supporting the biopsy cups formed as the distal parts of the treatment members 13A and 13B lest the biopsy cups should be displaced.

However, when the sleeve 11 and treatment members 13A and 13B are linked with one another by fitting the pivot pin 14 in the sleeve 11 and treatment members 13A and 13B and then forming the caulked sections 16, finishing must be carried out in order to match the outlines of the caulked sections 16 and the curved outer surface of the sleeve. When the caulked sections 16 have been formed, movement adjustment work must be carried out so that the treatment members 13A and 13B can move smoothly.

Figure 2A:
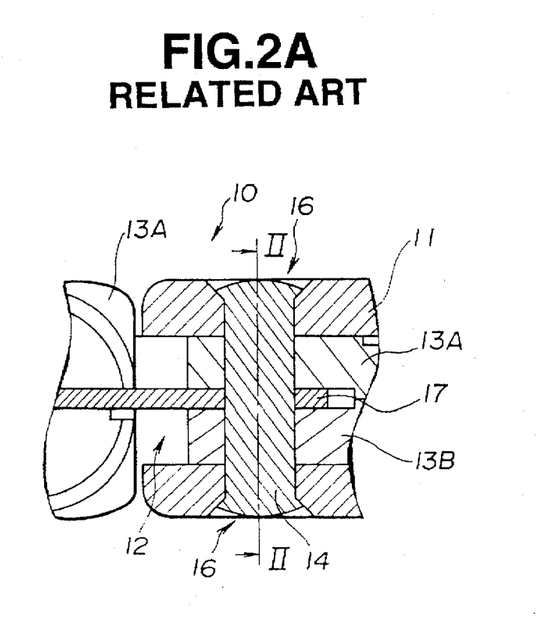
Figure 2B:
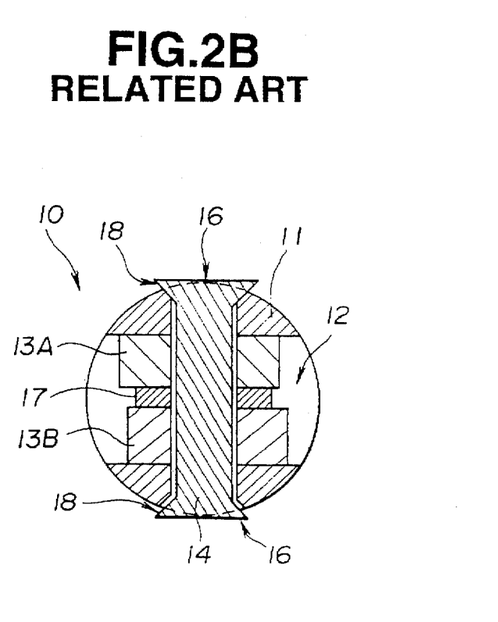

The foregoing sequence of work, which is required for forming the treatment unit 10 of treatment members 13A and 13B so that the treatment unit 10 can be opened or closed freely, is time-consuming and requires expertise. If the caulked sections 16 of the pivot pin 14 joining the treatment members 13A and 13B were insufficiently finished, when the endoscope-specific therapeutic instrument is repeatedly used, the pivot pin 14 would turn to change positions. As a result, at worst, the pivot pin 14 turns, as shown in FIGS. 2A and 2B, to change positions from the position shown in FIGS. 1A and 1B to a position angled by 90°. The caulked sections 16 having matched the curved outer surface of the sleeve 11 are displaced to appear as projections 18 projecting beyond the outer surface of the sleeve. With the appearance of the projections 18, there arises a possibility that when the endoscope-specific therapeutic instrument is inserted or removed, the projections 18 may damage the therapeutic instrument channel formed in the endoscope.

SUMMARY OF THE INVENTION

An object of the present invention is to provide a endoscope-specific therapeutic instrument that obviates the necessity of carrying out finishing after a pivot pin is fitted in a sleeve holding a treatment unit of the endoscope-specific therapeutic instrument.

Another object of the present invention is to provide a endoscope-specific therapeutic instrument in which a pivot pin fitted in a sleeve holding a treatment unit of the endoscope-specific therapeutic instrument does not turn to change positions and have any part thereof protruding.

Yet another object of the present invention is to provide an endoscope-specific therapeutic instrument in which when caulked sections are formed as parts of a sleeve holding a treatment unit of the endoscope-specific therapeutic instrument, imperfect rotation due to excessive caulking will not occur.

Briefly, an endoscope-specific therapeutic instrument in accordance with the present invention comprises a pair of treatment members, a sleeve having a slit in which the pair of treatment members is held, and a pivot pin for linking the pair of treatment members held in the sleeve with the sleeve so that the pair of treatment members can pivot freely. Both ends of the pivot pin lie in recesses, of which diameters are smaller than that of the surface of the sleeve, so as not to protrude beyond the outline of the sleeve.

Other features and advantages of the present invention will be fully apparent from the description below.

BRIEF DESCRIPTION OF THE DRAWINGS

FIGS. 1A to 2B show a treatment unit of a conventional endoscope-specific therapeutic instrument;

FIG. 1A is a sectional view showing the treatment unit in a direction of insertion;

FIG. 1B shows an I—I section of FIG. 1A;

FIG. 2A is a sectional view showing a state in which a pivot pin shown in FIG. 1A has rotated 90° to change positions;

FIG. 2B shows an II—II section of FIG. 2A;

FIGS. 3 to 9 relate to the first embodiment of the present invention;

FIGS. 8A and 8B show a IV—IV section of FIG. 7 containing a joint among treatment members and a sleeve;

FIGS. 10 to 11B relate to the second embodiment of the present invention;

FIGS. 11A and 11B show a V—V section of FIG. 7 containing a joint among treatment members and a sleeve;

DETAILED DESCRIPTION OF THE PREFERRED EMBODIMENTS

Referring to FIGS. 3 to 9, the first embodiment will be described.

To begin with, biopsy forceps that are an example of an endoscope-specific therapeutic instrument will be described with reference to FIGS. 3 and 4.

Figure 3:
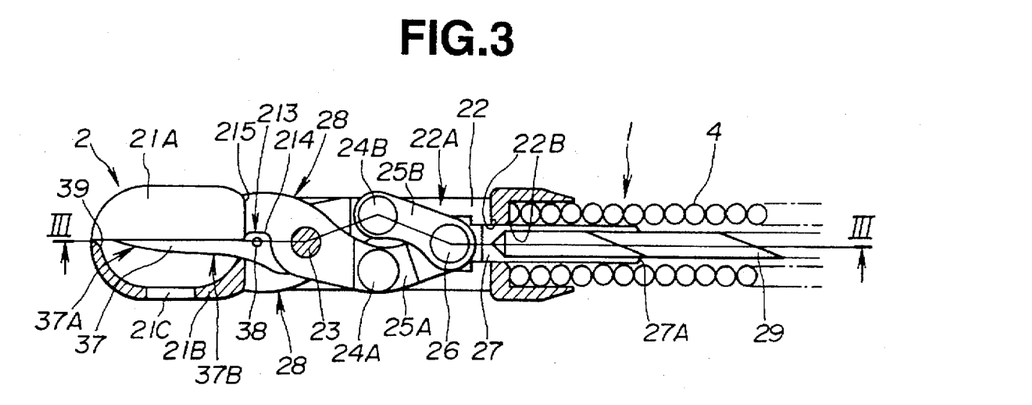
FIG. 3 is a sectional view schematically showing the structure of a treatment unit formed as the distal part of an endoscope-specific therapeutic instrument.
Figure 4:
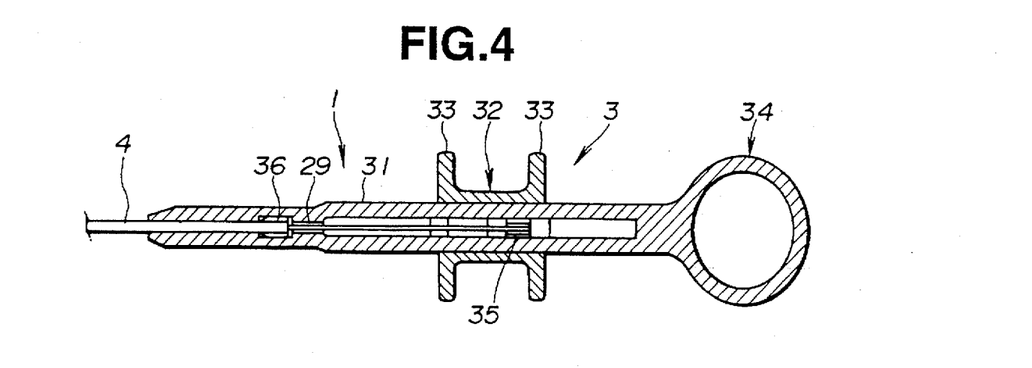
FIG. 4 is a sectional view schematically showing the structure of an operation unit formed as the proximal part of the endoscope-specific therapeutic instrument.

Biopsy forceps 1 shown in FIGS. 3 and 4 include a treatment unit 2 formed, as shown in FIG. 3, as the distal parts of the biopsy forceps 1, and an operation unit 3 formed, as shown in FIG. 4, as the proximal parts of the biopsy forceps 1. The treatment unit 2 and operation unit 3 are joined by means of a sheath 4 made of, for example, a closely-wound coil having plasticity, thus constructing the biopsy forceps 1.

The treatment unit 2 is constructed by placing a pair of treatment members 21A and 21B having biopsy cups, which are used for collecting living tissues or for treating a lesion, as the distal parts thereof in a slit 22A formed in a sleeve 22 fixed to the distal end of the sheath 4, and by linking the pair of treatment members 21A and 21B with the sleeve 22 by means of a pivot pin 23 so that the pair of treatment members 21A and 21B can pivot freely. The proximal ends of the treatment members 21A and 21B are linked with one end of each of arm members 25A and 25B by means of joint pins 24A and 24B so that the treatment members 21A and 21B can pivot freely. The other ends of the arm members 25A and 25B are coupled with a wire coupler 27 by means of a coupling pin 26 so that the arm members 25A and 25B can pivot freely.

In other words, the treatment members 21A and 21B held in the sleeve 22 are joined to each other by means of the pivot pin 23 so that the treatment members 21A and 21B can pivot freely. The treatment members 21A and 21B are linked with the arm members 25A and 25B by means of the joint pins 24A and 24B so that the treatment members can pivot freely. The arm members 25A and 24B are coupled with the wire coupler 27 by means of the coupling pin 26 so that the arm members can pivot freely. Thus, a pantographic mechanism is materialized, whereby when the wire coupler 27 advances or withdraws in an axial direction, the biopsy cups formed as the distal parts of the treatment members 21A and 21B open or close. Because of the pantographic mechanism, as shown in FIG. 5, the treatment members 21A and 21B are opened with the advancement of the wire coupler 27 toward the distal end of the biopsy forceps, and closed with the withdrawal of the wire coupler 27 toward the proximal end of the biopsy forceps.

Figure 5:
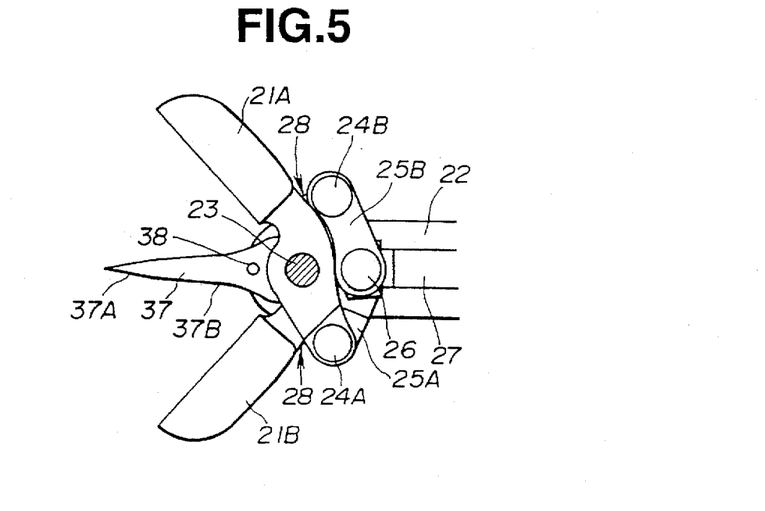
FIG. 5 shows treatment members that are open.

As shown in FIG. 5, a joint 28 between the proximal parts of the treatment members 21A and 21B and the arm members 25A and 25B is offset with respect to the axis of the biopsy forceps in an effort to retain the opening defined by the treatment members 21A and 21B at a certain width and to prevent the therapeutic instrument channel from being damaged.

An operation wire 29 extending from the wire coupler 27 shown in FIG. 3 lies through the sheath and is locked in a slider 32 that is clamping an axis 31 of the operation unit 3 shown in FIG. 4 so as to slide freely over the axis 31. Both ends of the slider 32 are formed as finger rests 33 that are supported by surgeon's index and middle fingers. Reference numeral 35 denotes a stopper for locking the operation wire 29 firmly in the slider 32. 36 denotes a stopper for firmly locking the sheath 4 in the operation unit 3. The stoppers are secured by injecting solder into the spaces between the stoppers and the wire and sheath.

A surgeon puts his/her thumb in a finger ring 34 formed behind the slider 32, supports the finger rests 33 of the slider 32 by his/her index and middle fingers, and then advances and withdraws the slider 32 in axial directions so as to move the wire 29 locked in the slider 32 in axial directions. With the movements of the wire 29 in axial directions, the wire coupler 27 attached to the distal end of the wire 29 is advanced and withdrawn in axial directions. The arm members 25A and 25B as well as the treatment members 21A and 21B, which constitute the pantographic mechanism, pivot so as to open and close the biopsy cups formed as the distal parts of the treatment members 21A and 21B.

When the coupler 27 withdraws because the wire 29 is pulled back, a back end 27A of the coupler should move smoothly in axial directions without being caught by the coil forming the sheath 4. The back end 27A is therefore chamfered. Likewise, the sleeve 22 has a chamfered section 22B so as not to engage with the wire coupler 27.

Reference numeral 37 denotes a needle for supporting the biopsy cups lest the biopsy cups should be displaced from a target lesion. 38 denotes a pin for fixing the needle 37 to the sleeve. The needle 37 has a two-stepped tapered surface including a tapered surface 37A and a tapered surface 37B. The taper angle of the tapered surface 37A is greater than that of the taper surface 37B. This dual taper angle contributes to an increase in strength of the needle 37.

The biopsy cups formed as the distal parts of the treatment members 21A and 21B have through-holes 21C for use in discharging body fluid. This is intended to increase the number of collected living tissues.

As shown in FIG. 3, a blade 39 for use in collecting living tissues is formed along each of the distal ends of the biopsy cups. The angle of the blade 39 with respect to the axis of the biopsy forceps ranges from 30° to 60°, thus permitting easy cutting of living tissues.

Figure 6:
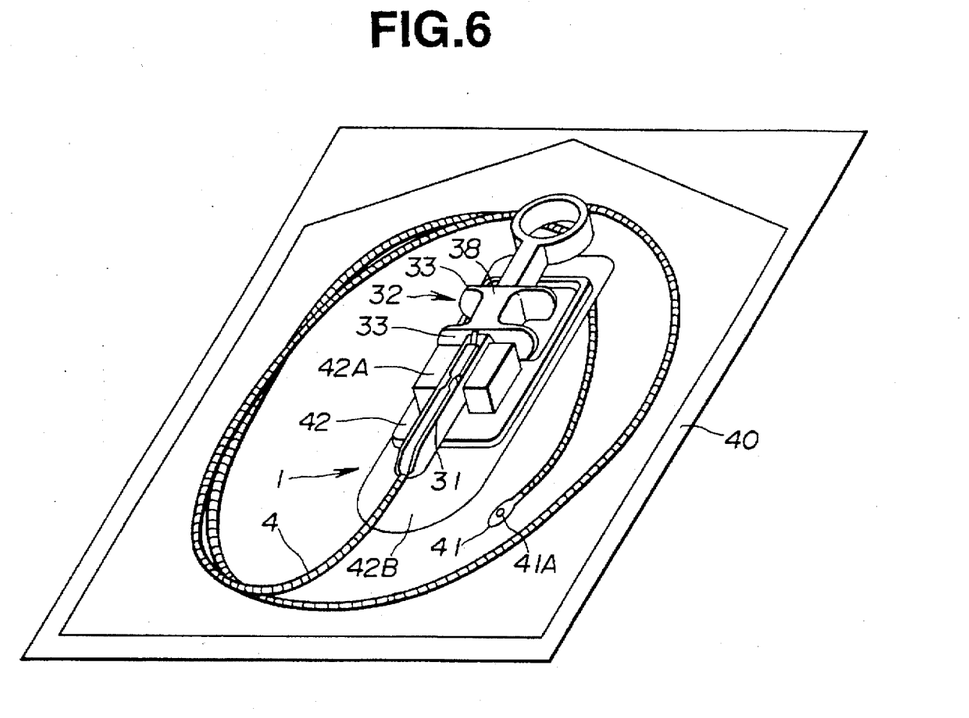
FIG. 6 is an oblique view showing a pack of unused biopsy forceps which an example of an endoscope-specific therapeutic instrument.

As shown in FIG. 6, the slider 32 has planes which are perpendicular to the finger rests 33 and whose sections look like a square with now rounded corners.

Figure 7:
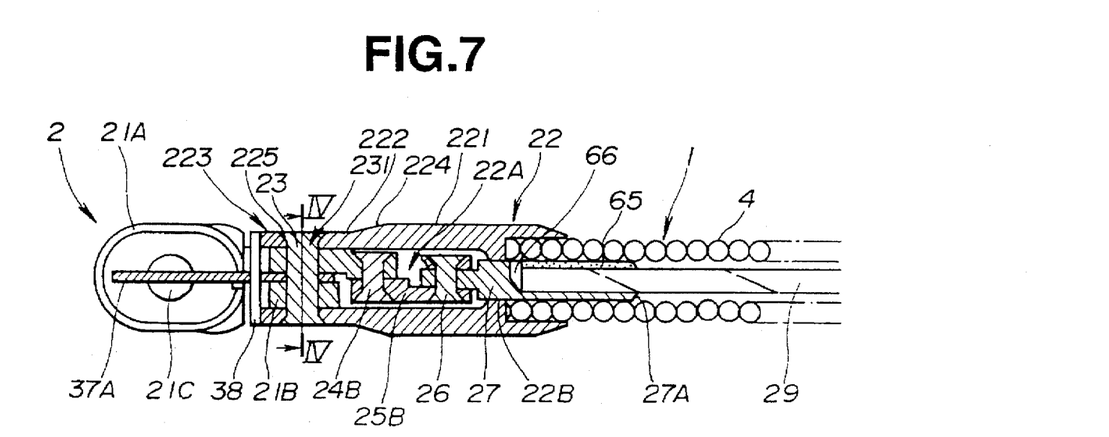
FIG. 7 shows a III—III section of FIG. 3.
Figure 8A:
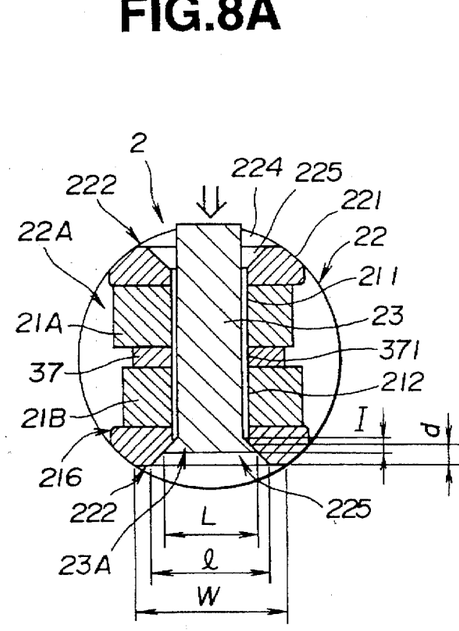
FIG. 8A shows the relationships among a pivot pin not having caulked sections, treatment members, and a sleeve.
Figure 8B:
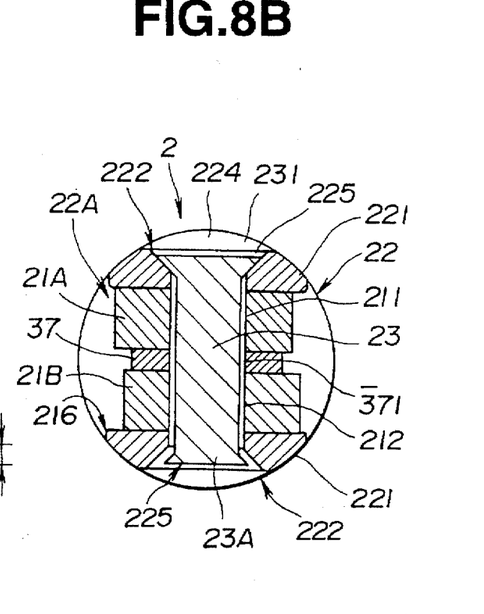
FIG. 8B shows the relationships among the pivot pin having caulked sections, treatment members, and sleeve.

Referring to FIGS. 7, 8A and 8B, the joint containing the treatment members 21A and 21B, sleeve 22, and pivot pin 23 will be described.

As shown in FIGS. 7 and 8B, the sleeve 22 is composed of a back portion 221 shaped substantially like a cylinder, and a front portion 223 that has two parallel planes 222 perpendicular to the axis of the pivot pin 23 and that is lowered relative to the outline of the back portion 221. Chamfered sections 224 are formed between the planes 222 of the front portion 223 and the cylindrical back portion 221, whereby the sleeve 22 appears as a streamlined unit. Through-holes in which the pivot pin 23 is inserted are bored in the planes 222, and countersinks 225 are formed in the outer surfaces of the planes 222.

Now, a procedure of linking the treatment members 21A and 21B with the sleeve 22 will be described.

First, the treatment members 21A and 21B having the biopsy cups as the distal parts thereof are placed in a slit 22A formed in the sleeve 22. The pivot pin 23 is then fitted in through-holes 211 and 212 bored in the sleeve 22 and treatment members 21A and 21B. The pivot pin 23 is caulked so that the treatment members 21A and 21B can pivot, thus producing a caulked section 231. The treatment members 21A and 21B are now linked with the sleeve 22. At this time, the end surface of the caulked section 231 is made flat to prevent the caulked section 231 from protruding beyond the countersink 225 formed in the plane 222. The pivot pin 23 in this embodiment has a flat countersunk head 23A at one end.

More particularly, as shown in FIG. 8A, first, the treatment member 21A, needle 37, and treatment member 21B are placed in that order at a given position in the slit 22A formed in the sleeve 22. The pivot pin 23 with a flat countersunk head is inserted into the countersink 225 formed in the plane 222 of the front portion 223 of the sleeve 22, the through-hole 211 bored in the treatment member 21A, a through-holes 371 bored in the needle 37, the through hole 12 bored in the treatment member 21B, and the countersink 225 formed in the other plane 222 of the front portion 223 of the sleeve 22 in that order.

The plane surface of the flat countersunk head 23A of the pivot pin 23 is subjected to pressure so that the slope of the flat countersunk head 23A will match the slope of the countersink 225. The tip of the pivot pin 23 is deformed in a direction of an arrow using a hammer, a caulking jig, or a laser, whereby the caulked section 231 shown in FIG. 8B is formed. At this time, the end surface of the caulked section 231 formed as the tip surface of the pivot pin 23 is evened, and the plane of the caulked section 231 is leveled even with or below to the plane surface 222 formed on the front portion 223 of the sleeve 22.

As for the dimensions of the flat countersunk head 23A of the pivot pin 23 and of the countersink 225 formed in the plane surface 222, assuming that the outer diameter of the flat countersunk head 23A is L, the height of the flat countersunk head 23A is H, the outer diameter of the countersink 25 formed in the plane surface 222 is 1, and the depth of the countersink 25 is d, the dimensions have the relationships of $L<1$ and $H<d$. The relationships are also true for the dimensions of the caulked section 231 and the countersink 225. The width W of the hole in the plane surface 222 formed on the sleeve 22 and the outer diameter L of the flat countersunk head 23A have the relationship of $L<W$.

The biopsy forceps 1 are, as shown in FIG. 6, sealed with a sterilization pack 40 when they are unused. At this time, the treatment members 21A and 21B are encased in a cap 41 having a transverse hole 41A. The operation unit 3 is mounted on a locking plate 42 that is composed of bosses 42A between which an axis 31 is interposed, and a tongue 42B extending from the the distal end of the axis 31. Since the operation unit 3 has the planes 38, the operation unit 3 is stably mounted on the locking plate 42. Besides, the sterilization pack sealing the biopsy forceps 1 does not swell very much and is prevented from breaking.

The operation of the biopsy forceps 1 having the aforesaid components will be described.

Figure 9:
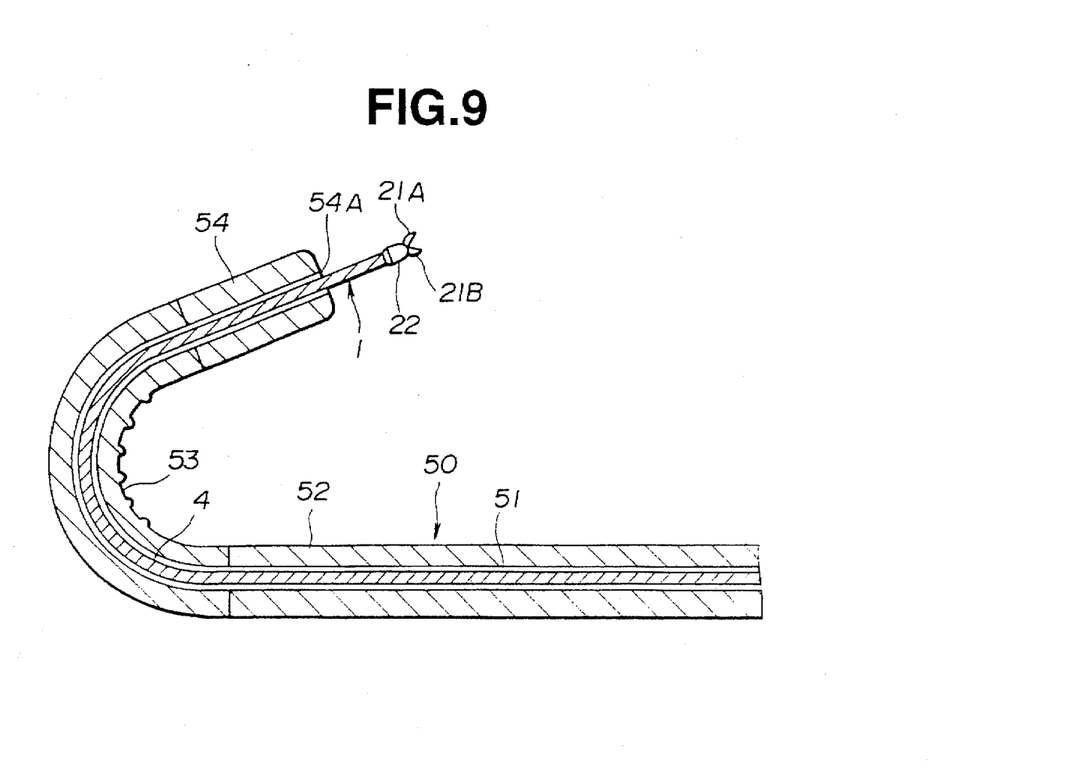
FIG. 9 shows an endoscope-specific therapeutic instrument lying through a therapeutic instrument channel in an endoscope.

To begin with, as shown in FIG. 9, the biopsy forceps 1 are inserted into a therapeutic instrument channel 51 in an endoscope 50 that has been placed in a human body. At this time, the biopsy forceps 1 runs through a flexible tube 52 of the endoscope, a bending section 53 thereof, and a distal structure 54 thereof, and then projects from a distal opening 54A thereof. While observing a view provided by an observation optical system of the endoscope, a surgeon places the biopsy cups formed as the distal parts of the treatment members 21A and 21B serving as the distal portions of the biopsy forceps 1 in a desired position.

The surgeon then puts his/her thumb into the finger ring 34 of the operation unit 3 and holds the slider 32 with his/her index and middle fingers. The surgeon then moves the slider 32 forward along the axis 31 using the index and middle fingers with the thumb as a supporting point. The operation wire 29 lying within the sheath starts moving forward, thus advancing the wire coupler 27 fixed to the distal end of the wire 29 toward the tips of the biopsy forceps. With the movement of the wire coupler 27, the arm members 25A and 25B and the treatment members 21A and 21B, which constitute a pantographic mechanism, pivot to open the biopsy cups formed as the distal parts of the treatment members 21A and 21B. Eventually, the needle 37 projects.

The needle 37 then pierces an intended region so as to position the treatment members 21A and 21B lest the treatment members 21A and 21B be displaced relative to the treatment unit. The slider 32 held with the index and middle fingers with the thumb as a supporting point is pulled back along the axis 31. The operation wire 29 lying through the sheath starts moving backward, thus withdrawing the wire coupler 27 attached to the distal end of the wire 29 along the axis. With the movement of the wire coupler 27, the arm members 25A and 25B and the treatment members 21A and 21B, which constitute a pantographic member, pivot to close the biopsy cups formed as the distal parts of the treatment members 21A and 21B. Consequently, living tissues are collected.

With the biopsy cups closed, the biopsy forceps 1 are removed from the human body and endoscope 50.

As long as an endoscope-specific therapeutic instrument is designed to be used repeatedly; such as, biopsy forceps with biopsy cups, is concerned, when treatment members are linked with a sleeve containing a treatment unit by means of a pivot pin with a flat countersunk head so that the treatment members can pivot freely, two plane surfaces are formed in parallel with each other as parts of the outer surface of the sleeve, and through-holes into which the pivot pin is fitted are bored in the planes perpendicularly to the planes. A countersink is formed at an entrance of each of the through-holes of the plane surface so that the outer diameter L of the flat countersunk head of the pivot pin and height H thereof, and the outer diameter 1 of the countersink and depth d thereof have the relationships of L<1 and H<d. The width W of each of the holes formed in the plane surfaces on the sleeve and the outer diameter L of the flat countersunk head are determined to have the relationship of L<W. The flat countersunk head of the pivot pin is fitted in one of the countersinks. The tip of the pivot pin is caulked so that the resultant caulked section will stay in the other countersink formed in the sleeve but not project from the plane. The treatment members are linked with the sleeve so that they can pivot freely. Therefore, even if the pivot pin, which supports the treatment members so that the treatment members can pivot freely, turns to change positions, the flat countersunk head of the pivot pin will not project from the plane formed as part of the outer surface of the sleeve. Thus, the endoscope-specific therapeutic instrument will not damage either the therapeutic instrument channel of the endoscope or the living tissues.

All that matters for caulking of the tip of the pivot pin is to create a plane surface on the flat countersunk head of the pivot pin. That is to say, while the flat countersunk head of the pivot pin is immobilized, a plane surface is created so that the tip of the pivot pin becomes substantially level with or lower than a plane surface formed as part of the sleeve. Thus, workability is excellent. Finishing becomes unnecessary. Moreover, a stable caulked section can be readily created. Man-hours can therefore be reduced. An inexpensive endoscope-specific therapeutic instrument can be provided.

A joint between treatment members and arm members and a joint between link plates are structured mutually similarly; that is, designed to pivot freely. Thus, man-hours can be decreased drastically, and a pantographic mechanism that can pivot smoothly and stably can be materialized at low cost.

Figure 10:
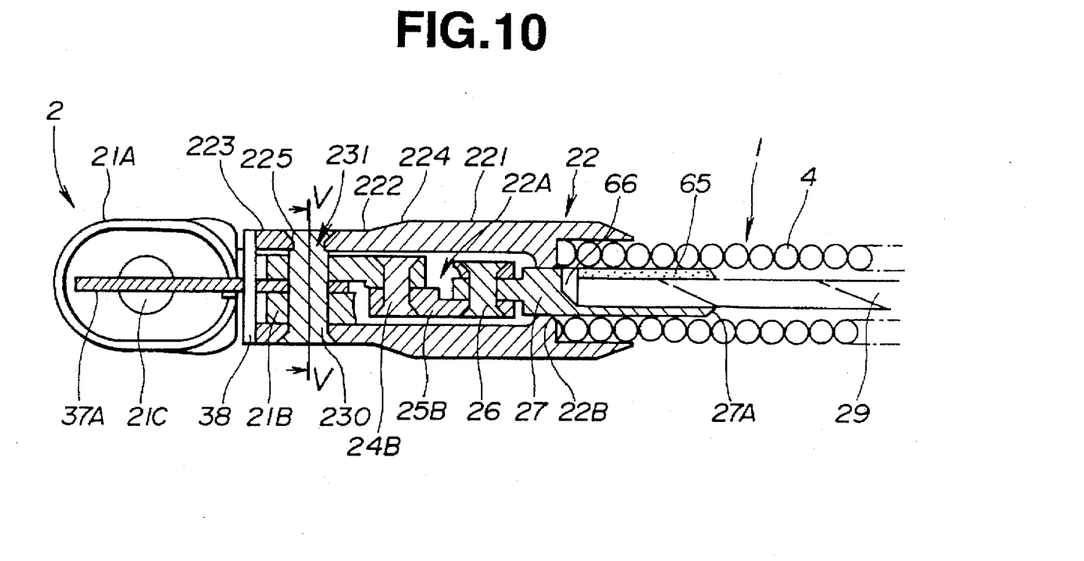
FIG. 10 is a sectional view of an endoscope-specific therapeutic instrument in which a pivot pin having a different structure is inserted.
Figure 11A:
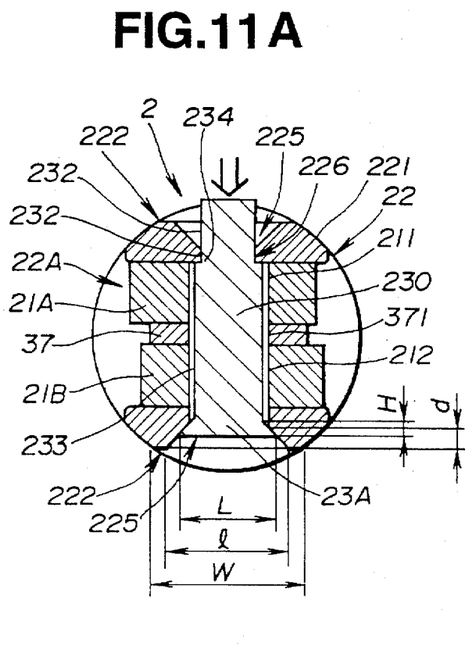
FIG. 11A shows the relationships among a pivot pin having a different structure but not having caulked sections, treatment members, and a sleeve.
Figure 11B:
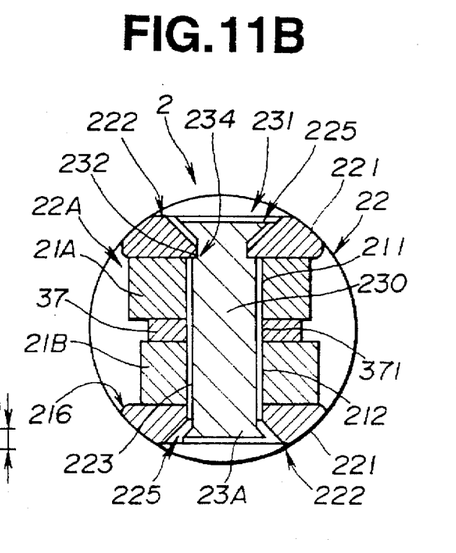
FIG. 11B shows the relationships among the pivot pin having a different structure and caulked sections, treatment members, and sleeve.

Referring to FIGS. 10, 11A, and 11B, the second embodiment of the present invention will be described.

As shown in FIGS. 10, 11A, and 11B, a pivot pin 230 in this embodiment has a structure different from the pivot pin 23 in the first embodiment. The outline of the axis of the pivot pin 23 looks like a bar whose diameter is constant. By contrast, the pivot pin 230 is provided with a flat countersunk head and stepped; that is, the pivot pin 230 includes a small-diameter section 232 serving as the tip of the pivot pin 230 and a large-diameter section 233 having the flat countersunk head thereof. Through-holes into which the pivot pin is fitted are bored in planes 222 formed on the sleeve 22. One through-holes 226 into which the small-diameter section 232 opposed to the flat countersunk head is fitted has a smaller diameter. Countersinks 225 are formed at entrances of the through-holes.

A step 234 differentiating the small-diameter section 232 of the pivot pin 230 from the large-diameter section 233 thereof is formed at a position such as not to narrow a slit 22A formed in the sleeve 22. The width of the slit 22A is held larger than the thicknesses of the treatment members 21A and 21B and of the needle 37. The other components are identical to those in the first embodiment and assigned the same reference numerals. No mention will be made of the component members.

For linking the treatment members 21A and 21B with the sleeve 22, first, as shown in FIG. 11A, the treatment members 21A, needle 37, and treatment member 21B are placed in that order at a given position in the slit 22A formed in the sleeve 22. The stepped pivot pin 230 is fitted into a countersink 225 bored in the plane 223 of the sleeve 22, a through-hole 212 bored in the treatment member 21B, a through-hole 371 bored in the needle 37, a through hole 211 bored in the treatment member 21A, and the through-hole 226 bored in the plane 222 of the sleeve 22 in that order. The slope of the flat countersunk head 28A of the pivot pin 230 is matched with the slope of the countersink 225. The step 284 joining the large-diameter section 233 of the pivot pin with the small-diameter section thereof is abutted on a plane on the slit 22A formed in the sleeve 22. While the plane surface of the flat countersunk head 23A is being subjected to pressure, the tip of the small-diameter section of the pivot pin is deformed in a direction of an arrow using a hammer, caulking jig, or laser in order to produce the caulked section 281.

As shown in FIG. 11B, the pivot pin 280 is caulked and secured in such a manner that the plane surface 222 formed on the sleeve having the slit 22A is held by means of the step 234 joining the large-diameter section 233 of the pivot pin 230 with the small-diameter section 232 thereof as well as the caulked section 281. The step 234 lies at a position permitting a width that is greater than the thicknesses of the treatment members 21A and 21B and needle 87. When the caulked section 231 is to be produced, therefore, the slit 22A formed in the sleeve 22 will not be narrowed. This means that clearances are ensured among the treatment member 21A, needle 37, and treatment member 21B which are placed in the slit 22A. The treatment unit 2 is thus constructed to be capable of pivoting freely. The other operation is identical to that of the first embodiment.

As mentioned above, a step differentiating a large-diameter section of a pivot pin from a small-diameter section thereof is formed in a pivot pin. The step is located at a given position of the pivot pin lest a slit formed in a sleeve should be narrowed during caulking. This structure helps simplify the caulking work. Moreover, since the step of the pivot pin holds the sleeve having the slit, the slit is not narrowed. Movement adjustment work need not be performed in a process succeeding caulking. An endoscope-specific therapeutic instrument having excellent operability can be provided. The other advantages are identical to those of the first embodiment.

Figure 12:
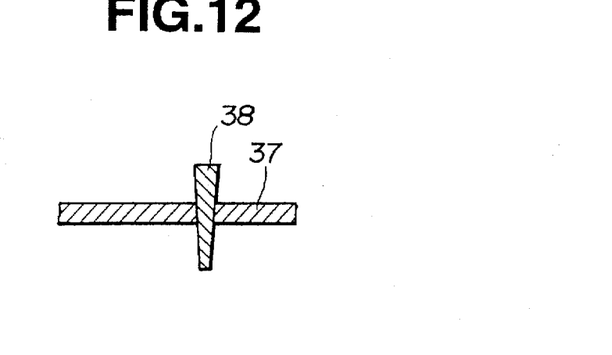
FIG. 12 shows a section of a securing pin for securing a needle.

As shown in FIG. 12, a pin 38 is used to secure the needle 37 to the sleeve 22 constituting the treatment unit 2. Thus, the needle 37 piercing an intended region is prevented from swaying. The pin 38 is tapered, so that the diameter of the pin 38 becomes smaller gradually toward the tip thereof. The tapered pin 38 is pressured and fitted into a through-hole bored in the needle 37. At this time, as shown in FIG. 13, both ends of the pin 38 are firmly locked in notches 22C formed in the sleeve 22, whereby the pin 38 is prevented from swaying.

An escape recess 213 is, as shown in FIG. 3, formed in each of the treatment members 21A and 21B, so that the escape recesses 213 arch over around the pin 38. Ridges 214 and 215 are rounded. Thus, concentration of stress on the treatment members 21A and 21B is dispersed.

Figure 13:
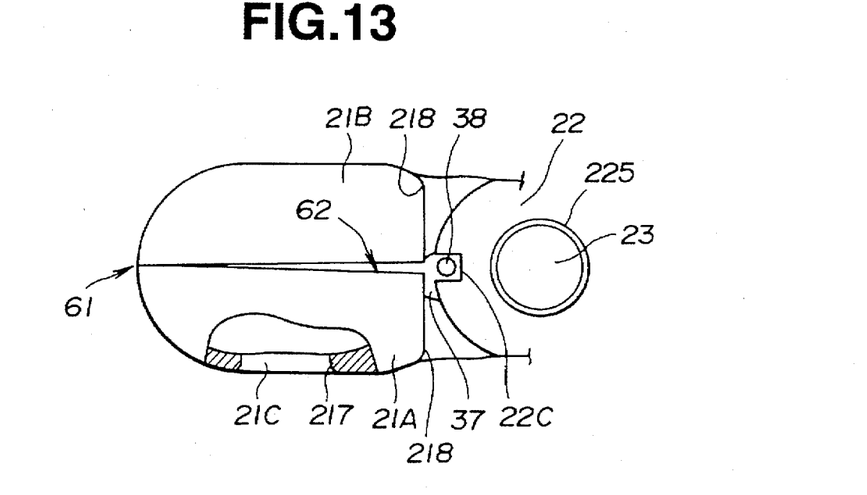
FIG. 13 is an arrow-pointed view of FIG. 7 showing the tips of biopsy cups in details.

As shown in FIG. 13, the biopsy cups have a space 62 between them. The space 62 gets wider gradually from the distal end of the space to the proximal end thereof, so that the tips 61 of the biopsy cups formed as the distal parts of the treatment members 21A and 21B bite each other accurately. Due to the presence of the space 62, when the biopsy cups formed as the distal parts of the treatment members 21A and 21B are closed, the tips 61 of the biopsy cups bite each other without causing a gap. Consequently, the biopsy cups can collect living tissues reliably.

Figure 14:
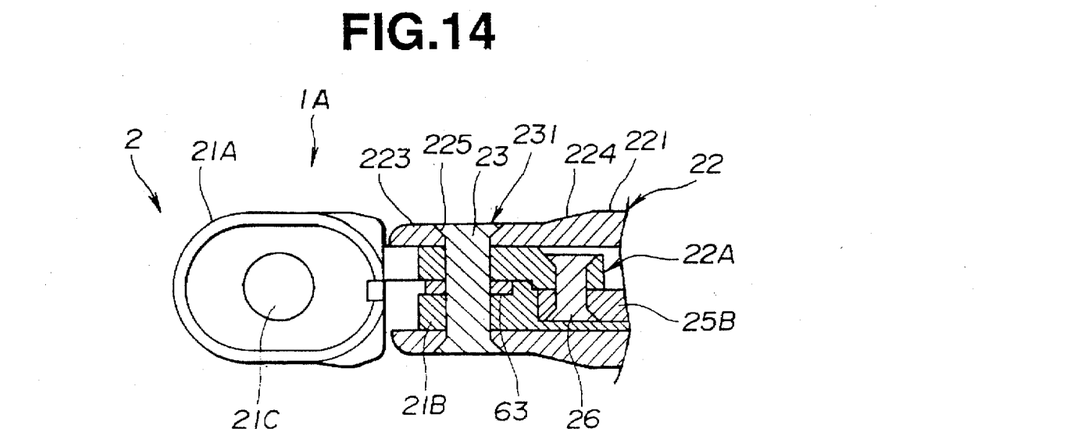
FIG. 14 is a sectional view schematically showing the structure of a treatment unit without a needle.

The biopsy forceps 1 are not limited to the aforesaid type of biopsy forceps with a needle. As shown in FIG. 14, biopsy forceps 1A without a needle will do. However, when the needle 37 is removed from the biopsy forceps 1, a gap corresponding to the thickness of the needle 37 is created between the treatment members 21A and 21B in the slit 22A formed in the sleeve 22. The creation of the gap prevents the treatment members 21A and 21B from pivoting smoothly. For overcoming this drawback, when the biopsy forceps 1A without a needle is constructed, a spacer 63 having the same thickness as the needle 37, as shown in FIG. 14, replaces of the needle 37 so that the slit will be occupied by the same width as it is when the needle 37 is included. The other components are identical to those of the first embodiment, and assigned the same reference numerals. No mention will be made of the same component members.

As mentioned above, either biopsy forceps without a needle or biopsy forceps with a needle can be constructed by employing a spacer or a needle. The component parts other than the needle and spacer can be shared by the biopsy forceps without a needle and the biopsy forceps with a needle.

Figure 15:
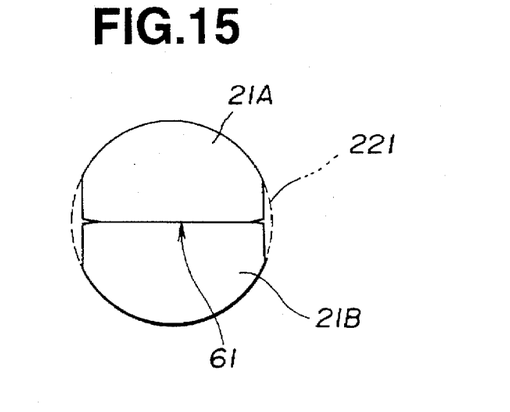
FIG. 15 is a front view showing biopsy cups.
Figure 16:
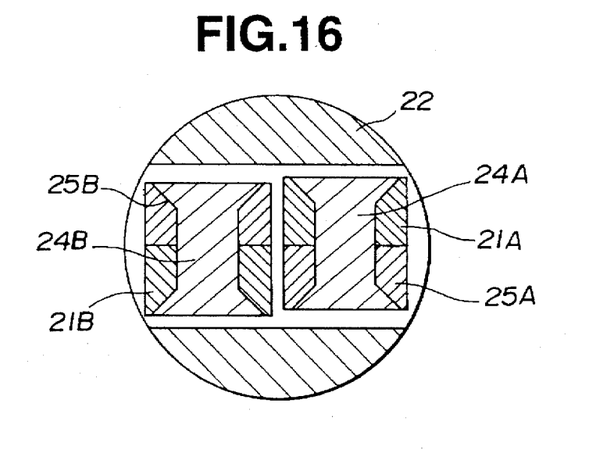
FIG. 16 is a front sectional view showing a joint between treatment members and arm members.

When the biopsy forceps are inserted into a therapeutic instrument channel lying through an endoscope, the treatment unit of the biopsy forceps may come into contact with the therapeutic instrument channel and damage it. For protecting the therapeutic instrument channel, as shown in FIG. 8B, the ridges soaring to the slit 22A formed in the sleeve 22 are chamfered, or more particularly, rounded or curved, to appear as chamfered sections 216. As shown in FIG. 13, the outer circumferences of the through-holes 21C in the biopsy cups and the ridges of the biopsy cups are rounded to appear as chamfered sections 217 and 218. Moreover, as shown in FIG. 15, the tips 61 of the biopsy cups may be notched so that the tips 61 will lie inward of the outer circumference of the back portion 221 of the sleeve in which the treatment members 21A and 21B are placed. Alternatively, as shown in FIG. 16, the joint containing the treatment members 21A and 21B and the arm members 25A and 25B is made smaller than the outline of the sleeve 22, thus protecting the therapeutic instrument channel from damage.

An adhesive 65 may be used to attach and fix the operation wire 29 to the wire coupler 27 or the sheath 4 containing the operation wire 29 to the sleeve 22. In this case, the outer circumference of the sheath 4 need not be cut. If only the adhesive 65 is applied, since the adhesive 65 invades into the gaps of the coil of the sheath 4, fixation is achieved readily and highly intensively. This results in a reduction in the expenses of facilities used for laser welding, brazing, or other fixation and a decrease in man-hours required for the fixation. Eventually, an inexpensive therapeutic instrument is made available. When a through-hole 66 communicating with a through-hole, which is bored in the coupling member 27 and through which the operation wire 29 is routed, is bored in the junction between the coupling member 27 and operation wire 29, cutting lubricant used for machining parts can be readily washed away. Besides, gas generated from the adhesive during hardening of the adhesive can be escaped through the through hole 66. The adhesive strength therefore remains stable. The through-hole 66 is formed to communicate with the deepest end of the operation wire routing hole formed in the coupling member 27, whereby accumulation of cutting lubricant or shavings can be prevented.

Figure 17:
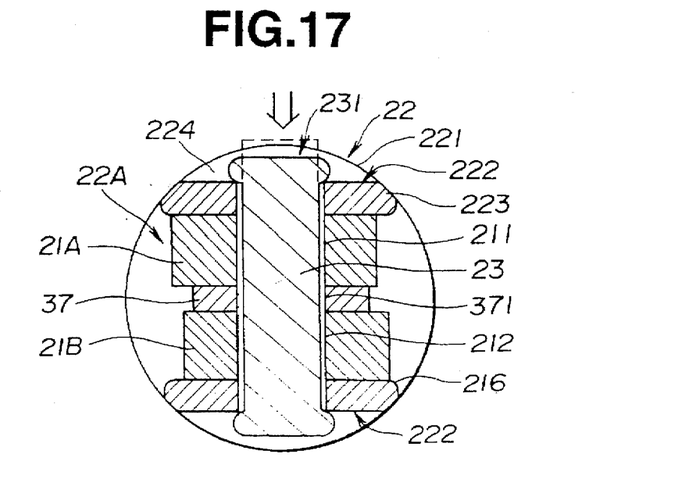
FIG. 17 is a sectional view showing another structure including treatment members joined by means of a pivot pin and a sleeve.
Figure 18:
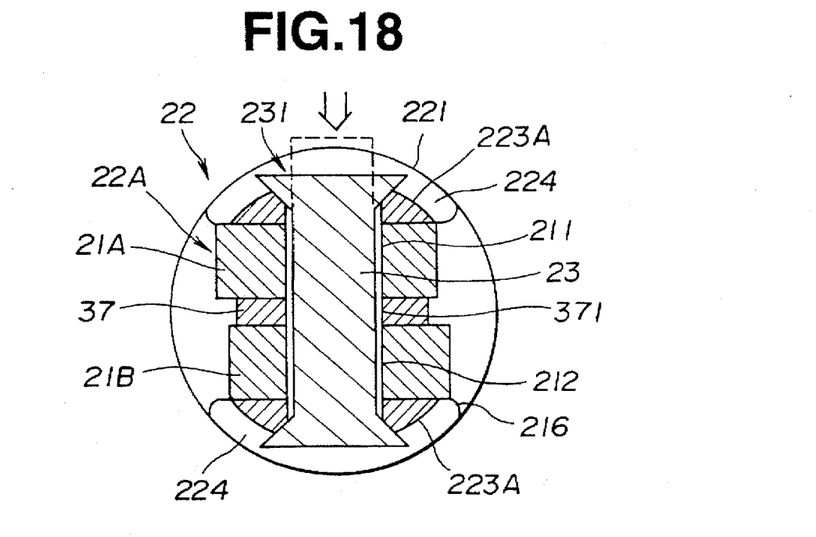
FIG. 18 is a sectional view showing yet another structure including treatment members joined by means of a pivot pin and a sleeve.

In the aforesaid embodiment, the flat countersunk head 23A of the pivot pin and the caulked section 231 are stowed in the countersink formed in the plane 22 on the front portion 223 of the sleeve 22. If a space in which the countersink is formed is not affordable because of the small dimensions of an endoscope-specific therapeutic instrument, as shown in FIG. 17, no countersink may be formed in the plane 222 on the front portion 223 of the sleeve 22 but the flat countersunk head 23A of the pivot pin 23 and the caulked section 231 may be arranged so that they will not protrude beyond the outline of the large-diameter back portion 221. Alternatively, as shown in FIG. 18, a small-diameter front portion 223A having a rounded surface may be formed instead of the plane 222 on the front portion 223 of the sleeve 22. The flat countersunk head 23A of the pivot pin 23 and the caulked section 231 may be arranged over the rounded surface of the small-diameter front portion 223A so that they will not protrude beyond the outline of the large-diameter back portion 221.

For reliably locking the operation wire 29, which lies through the sheath 4, in the operation unit 3 as shown in FIG. 4, the stopper 35 is attached to the back end of the wire. For reliably locking the sheath 4 in the operation unit 3, the stopper 36 is attached to the back end of the sheath 4. For fixing the stoppers 35 and 36 to the operation wire 29 and sheath 4 respectively, solder is injected into spaces between the stoppers 35 and 36 and between the operation wire and the stopper 35.

Figure 19:
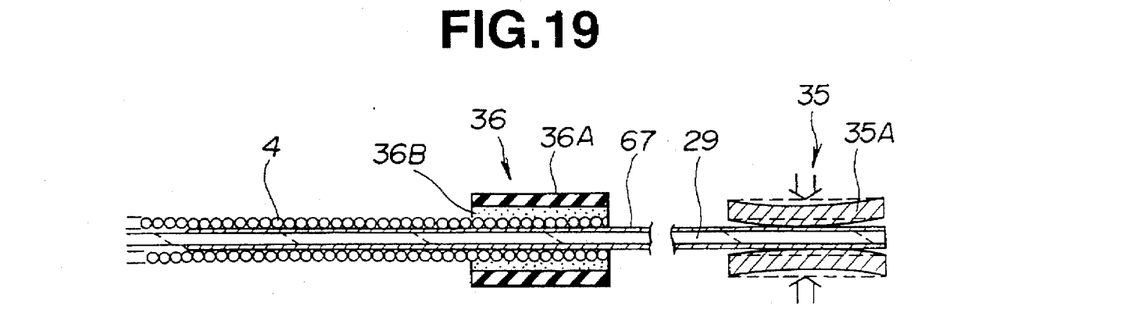
FIG. 19 is an explanatory diagram concerning a stopper attached to the back ends of a sheath and a wire.

However, it is time-consuming to inject solder in order to fix the operation wire 29 to the stopper 35. There is an increasing demand for a simple procedure of fixing them. As shown in FIG. 19, the whole circumference of the proximal part of the operation wire 29 lying through the sheath, which is located in the operation unit, is enclosed with an enforcement pipe 67. The back end of the enforcement pipe 67 is enclosed with a fixation pipe 35A used to realize the stopper 35. The substantially center part of the fixation pipe 35A is caulked as indicated with arrows, whereby the fixation pipe 35 is integrated together with the enforcement pipe 67 into the wire 29. Thus, the stopper 35 is formed at the back end of the operation wire 29.

In the past, the back end of the sheath 4 has been cut by means of a cutter so that the cut section will be smooth. For simplifying the work, a nipper is used to cut the back end of the sheath 4, and the back end is enclosed with a heat contractive tube 36A that is made of a thermoplastic resin such as an olefin resin and that is provided with an adhesive layer 36B. Thus, the stopper 36 is constructed. The melting point of the adhesive layer 36B is less than that of the heat contractive tube 36A overlying the adhesive layer 36B. When the heat contractive tube 36A is heated, therefore, the adhesive layer 36B having a lower melting point melts earlier. This causes the inner diameter of the heat contractive tube 36A to shrink. The adhesive layer therefore flows over the entire circumference of the sheath 4, and the heat contractive tube 36A contracts as a result of the heat. Thus, sufficient fixing intensity is exerted.

As mentioned above, when a heat contractive tube is made of an olefin resin that is a thermoplastic resin, reliable adhesive fixation can be achieved at a low temperature. The proximal part of an operation wire is enclosed with an enforcement pipe, and the enforcement pipe is enclosed with a fixation pipe. The fixation pipe and enforcement pipe are caulked together and integrated into the operation wire, whereby a reliable stopper can be readily realized. When the enforcement pipe is coated, buckling of the operation wire within the operation unit can be readily prevented.

Figure 20:
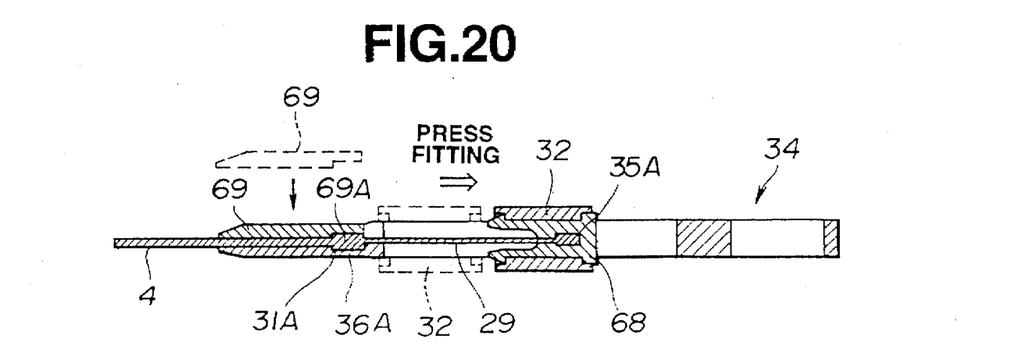
FIG. 20 is a sectional view showing assembled components of an operation unit.

As shown in FIG. 20, a presser 68 having the fixation pipe 35A inserted longitudinally is pressed into the slider 32. The heat contractive tube 36A is held in a recess 69A formed in a plate 69 and in a recess 31A formed in the axis 31. The plate 69 is pressed into the axis 31.

Figure 21:
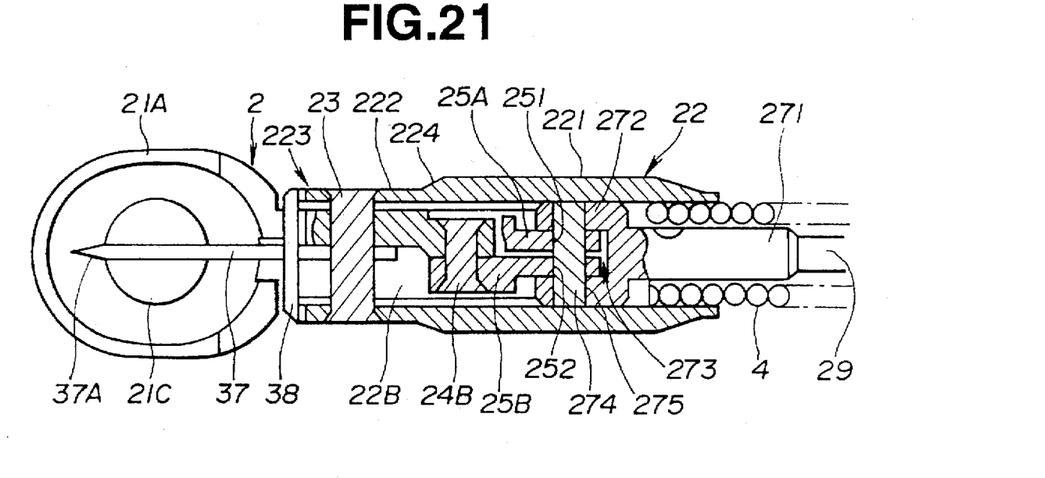
FIG. 21 is a sectional view showing another structure of a treatment unit.

As shown in FIG. 21, in this embodiment, the joint between the arm members 25A and 25B and the wire coupler 27 has a structure different from the one in either the first or second embodiment. Specifically, as illustrated, the arm members 25A and 25B are held in a slit 273 in a large-diameter section 272 formed as the distal part of a wire coupler 271, and linked with the wire coupler 271 by means of a pin 274, similarly to the treatment members 21A and 21B, so that the arm members 25A and 25B can pivot freely.

In other words, the proximal parts of the arm members 25A and 25B are placed in the slit 273 formed in the wire coupler 271. In this state, the pin 274 is fitted into securing-pin routing holes 251 and 252 bored in the proximal parts of the arm members 25A and 25B as well as a through hole 275 bored in the wire coupler 271, whereby the arm members 25A and 25B are linked with the wire coupler 271 so that they can pivot freely.

Figure 22:
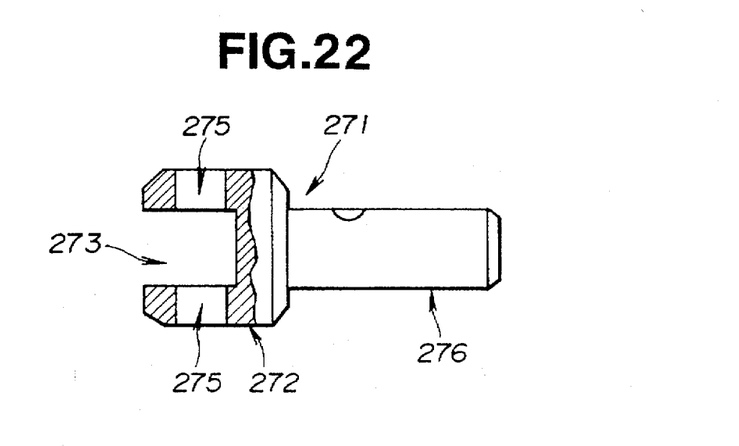
FIG. 22 is a partial sectional view showing another structure of a wire coupler.
Figure 23:
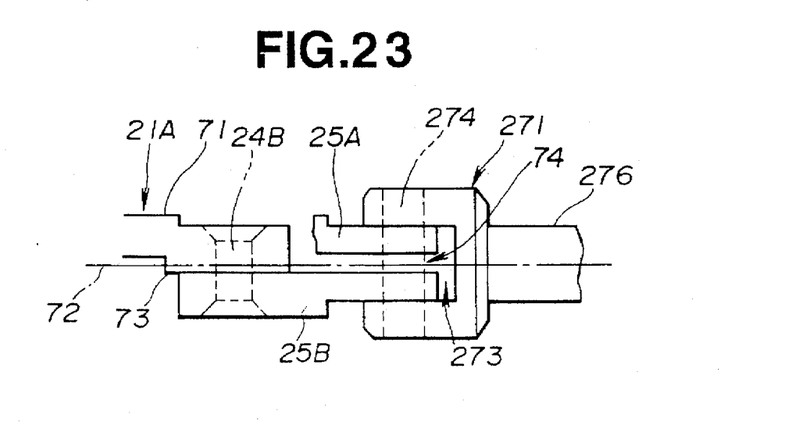
FIG. 23 shows the wire coupler in FIG. 22 with arm members attached.

As shown in FIG. 22, the wire coupler 271 consists of a large-diameter section 272 having planes extending in parallel with each other and a cylindrical small-diameter section 276. The slit 273 is formed in the large-diameter section 272. The through-hole 275 is transversing the slit 273 and penetrating perpendicularly through the two planes. As shown in FIG. 23, an arm 71 of the treatment member 21A has a thick step 73 extending beyond a center line 72 in FIG. 23. The step 73 is used as a joint between the treatment member 21A and arm member 25B. A gap 74 is interposed between the arm members 25A and 25B. The other components are identical to those of the aforesaid embodiment, and assigned the same reference numerals. No mention will be made of the same component members.

As mentioned above, since a gap is interposed between two arm members that used to be in close contact with each other, the arm members can pivot more smoothly and the pantographic mechanism operates more reliably. The other operation and advantages are identical to those of the previous embodiment. A countersink employed in the first embodiment may be formed to communicate with the through-hole 275 in the wire coupler 271. In this case, a pivot pin with a flat countersunk head resembling the one in the first embodiment is used as the pin 274. The tip of the pivot pin is then caulked in the same manner as in the first embodiment.

Figure 24:
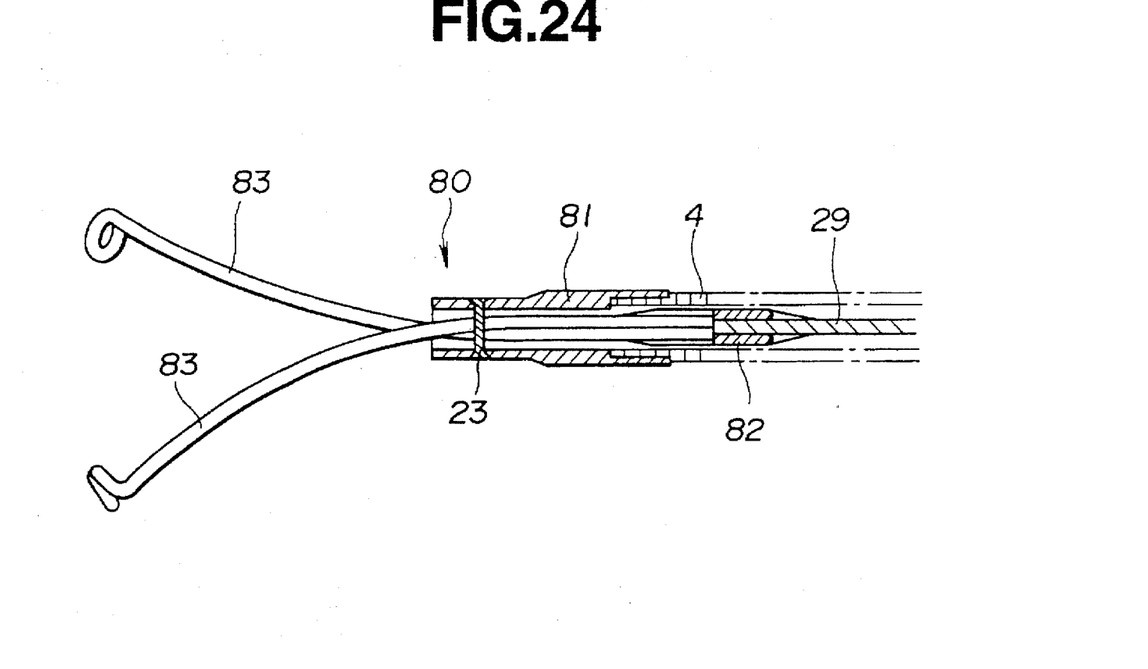
FIG. 24 is a sectional view schematically showing the structure including the distal parts of clamp forceps that are an example of an endoscope-specific therapeutic instrument.
Figure 25:
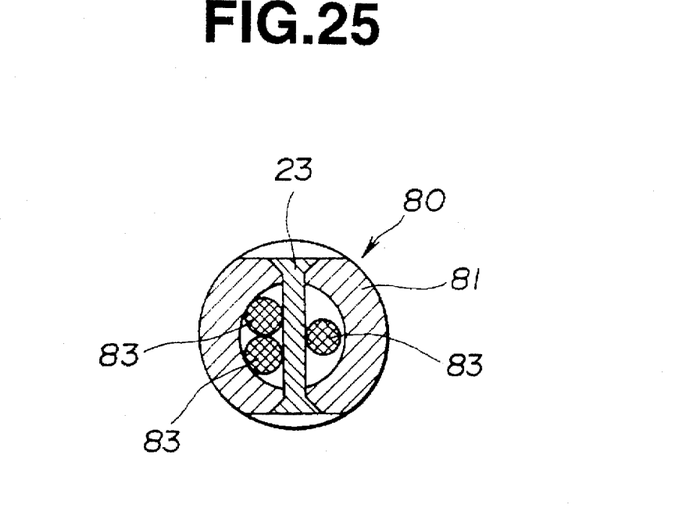
FIG. 25 is a sectional view showing a pivot pin fitted into the distal parts of the clamp forceps.

In the aforesaid embodiments, an endoscope-specific therapeutic instrument is biopsy forceps having a pair of treatment members whose distal parts are formed as biopsy cups and which can pivot freely. The therapeutic instrument is not limited to the biopsy forceps having biopsy cups as the distal parts thereof but may be any of various kinds of pairs of forceps capable of pivoting freely. For example, as shown in FIGS. 24 and 25, clamp forceps 80 will suffice. In the clamp forceps 80, a coupling member 82 is attached to the tip of the operation wire 29, and a plurality of clamping members 83 are fixed to the coupling member 82. When the operation wire 29 is advanced or withdrawn in a direction of insertion, the clamping members 83 fixed to the coupling member 82 open or close while sliding to project or sink. The number of clamping members is not limited to three.

In the present invention, it will be apparent that a wide range of different embodiments can be constituted on the basis of the invention without departing from the spirit and scope of the invention. This embodiment will be limited to the accompanying claims but not restricted to any specific embodiments.

What is claimed is:

1. An endoscope-specific therapeutic instrument, comprising:

a pair of treatment members;

a sleeve having a slit in which said pair of treatment members are held; and a pivot pin for linking said pair of treatment members held in said sleeve with said sleeve so that said pair of treatment members can pivot freely, each end of said pivot pin lying upon a respective recessed surface in said sleeve such that either end of said pivot pin does not protrude beyond an outer peripheral surface of said sleeve, wherein each said recessed surface is a planar surface formed perpendicularly to an axis of said pivot pin, each said planar surface having a hole into which one end of said pivot pin is fitted.

2. An endoscope-specific therapeutic instrument according to claim 2, wherein a caulked section is formed at at least one end of said pivot pin.

3. An endoscope-specific therapeutic instrument according to claim 2, said pivot pin is a stepped pivot pin having a large-diameter section and a small-diameter section.

4. An endoscope-specific therapeutic instrument according to claim 1, wherein said pivot pin has a flat countersunk head at one end.

5. An endoscope-specific therapeutic instrument according to claim 4, wherein at least one of said holes on said sleeve is a countersink having a shape which matches the shape of said flat countersunk head of said pivot pin.

6. An endoscope-specific therapeutic instrument according to claim 1 or claim 4, wherein said pivot pin is a stepped pivot pin having a large-diameter section and a small-diameter section.

7. An endoscope-specific therapeutic instrument according to claim 4, wherein a width of the planar surface having the flat countersunk head of said pivot pin thereon is greater than an outer diameter of said flat countersunk head of said pivot pin.

8. An endoscope-specific therapeutic instrument according to claim 4, wherein an outer diameter of said flat countersunk head of said pivot pin is less than an outer diameter of a countersink formed in the planar surface having the flat countersunk head of said pivot pin thereon, and a height of said flat countersunk head is less than a depth of said countersink.

9. An endoscope-specific therapeutic instrument according to claim 1, wherein a pair of arm members are linked with proximal ends of said pair of treatment members which are linked with said sleeve forming a treatment unit-by means of said pivot pin so that said pair of arm members can pivot freely, the other ends of said pair of arm members are linked with one end of a wire coupler the other end of which is coupled with a wire routed to an operation unit so that said pair of arm members can pivot freely, and said treatment unit opens or closes with the advancement or withdrawal of said wire coupler.

10. An endoscope-specific therapeutic instrument according to claim 9, wherein said pair of arm members are linked with said wire coupler by means of a pivot pin so that said pair of arm members can pivot freely.

11. An endoscope-specific therapeutic instrument according to claim 9, wherein said pair of arm members are held in a slit formed in said wire coupler, and linked with said wire coupler by means of a pin so that said pair of arm members can pivot freely.

12. An endoscope-specific therapeutic instrument according to claim 11, wherein a step formed on an arm of at least one of said treatment members is thicker than the rest said arm, and a gap is created between said arm members held in said slit formed in said wire coupler.

13. An endoscope-specific therapeutic instrument according to claim 9, wherein a stopper attached to an end of said wire is composed of an enforcement pipe for enclosing said wire and a stopper pipe for enclosing said enforcement pipe.

14. An endoscope-specific therapeutic instrument according to claim 9, wherein said wire linking said wire coupler and said operation unit lies within a sheath made of a coil.

15. An endoscope-specific therapeutic instrument according to claim 14, wherein a stopper attached to an end of said sheath is a heat contractive tube provided with an adhesive layer.

16. An endoscope-specific therapeutic instrument according to claim 15, wherein the melting point of said adhesive layer is lower than that of said heat contractive tube.

* * * * *